United States Patent
Lightcap et al.

(10) Patent No.: US 11,484,453 B2
(45) Date of Patent: Nov. 1, 2022

(54) AUTOMATED ORTHOSTATIC HYPOTENSION ASSESSMENT

(71) Applicant: Hill-Rom Services, Inc., Batesville, IN (US)

(72) Inventors: Kristen Keaton Lightcap, Cary, NC (US); Timothy Receveur, Apex, NC (US); Matthew Mccormick Riordan, Apex, NC (US); Eugene Urrutia, Durham, NC (US)

(73) Assignee: Hill-Rom Services, Inc., Batesville, IN (US)

( * ) Notice: Subject to any disclaimer, the term of this patent is extended or adjusted under 35 U.S.C. 154(b) by 313 days.

(21) Appl. No.: 16/935,678

(22) Filed: Jul. 22, 2020

(65) Prior Publication Data

US 2021/0030610 A1    Feb. 4, 2021

Related U.S. Application Data

(60) Provisional application No. 62/880,771, filed on Jul. 31, 2019.

(51) Int. Cl.
*A61G 7/057* (2006.01)
*A61G 7/05* (2006.01)
(Continued)

(52) U.S. Cl.
CPC .......... *A61G 7/057* (2013.01); *A61B 5/02405* (2013.01); *A61B 5/1102* (2013.01);
(Continued)

(58) Field of Classification Search
CPC ...... A61G 7/057; A61G 7/0507; A61G 7/052; A61G 2203/32; A61G 2203/44;
(Continued)

(56) References Cited

U.S. PATENT DOCUMENTS 7,612,681 B2   11/2009   Azzaro et al.
9,451,905 B2   9/2016   Op Den Buijs et al.
(Continued)

FOREIGN PATENT DOCUMENTS

WO   200241771 A1   5/2002
WO   2016034907 A1   3/2016
(Continued)

OTHER PUBLICATIONS

Rajagopalan, Ramesh., et al. "Fall Prediction and Prevension Systems: Recent Trends, Challenges, and Future Research Directions", Sensors (Basel, Switzerland), 17(11), 2509, 2017.
(Continued)

*Primary Examiner* — Robert G Santos
(74) *Attorney, Agent, or Firm* — Merchant & Gould P.C.

(57) ABSTRACT

A system for automatically assessing orthostatic hypotension for a patient supported on a patient support apparatus. The system receives position data identifying a first position of a patient supported on a patient support apparatus, and after a delay, receives vital signs data of the patient. The system receives position data identifying a second position of the patient supported on the patient support apparatus, and after a delay, receives vital signs data of the patient. The system determines an orthostatic hypotension assessment based on a difference in the vital signs data between the first and second positions. Based on the orthostatic hypotension assessment, the system modifies one or more conditions on the patient support apparatus to mitigate a risk for patient fall.

20 Claims, 8 Drawing Sheets

(51) Int. Cl.
  *A61B 5/024* (2006.01)
  *A61B 5/11* (2006.01)
  *A61B 5/318* (2021.01)

(52) U.S. Cl.
  CPC ............ *A61B 5/318* (2021.01); *A61G 7/0507* (2013.01); *A61G 2203/32* (2013.01); *A61G 2203/44* (2013.01)

(58) Field of Classification Search
  CPC ..... A61B 5/318; A61B 5/02405; A61B 5/024; A61B 5/1102; A61B 5/11
  USPC ............................................ 5/425, 424, 600
  See application file for complete search history.

(56) References Cited

U.S. PATENT DOCUMENTS

| | | | | |
|---|---|---|---|---|
| 10,124,172 | B2* | 11/2018 | Lyons | A61N 1/365 |
| 11,154,252 | B2* | 10/2021 | Meriheina | A61B 5/6801 |
| 2014/0358017 | A1* | 12/2014 | Op Den Buijs | A61B 5/02444 600/508 |
| 2015/0223761 | A1 | 8/2015 | Meriheina et al. | |
| 2016/0029904 | A1* | 2/2016 | Quinn | A61B 5/11 600/499 |
| 2016/0235610 | A1 | 8/2016 | Drake | |
| 2016/0331974 | A1 | 11/2016 | Lyons et al. | |
| 2018/0308336 | A1 | 10/2018 | Baker et al. | |
| 2021/0030610 | A1* | 2/2021 | Lightcap | A61G 7/05 |

FOREIGN PATENT DOCUMENTS

| | | | |
|---|---|---|---|
| WO | 2018223269 A1 | 12/2018 | |
| WO | 2019018167 A1 | 1/2019 | |
| WO | WO-2020096311 A1 * | 5/2020 | ............. A61B 5/021 |

OTHER PUBLICATIONS

Bauer, Paul, et al., "Modeling Bed Exit Likelihood in a Camera-Based Automated Video Monitoring Application", IEEE International Conference on Electro Information Technology (EIT), pp. 56-61, 2017.

White, N.J., "Heart-Rate Changes on Standing in Elderly Patients with Orthostatic Hypotension", Clinical Science, May 1, 1980, 58 (5) pp. 411-413, retrieved from http://www.clinsci.org/content/58/5/411.

"Tool 3F: Orthostatic Vital Sign Measurement", Agency For Healthcare Research and Quality, Accessed Jul. 6, 2019 from https://www.ahrq.gov/professionals/systems/hospital/fallpxtoolkit/fallpxtk-tool3f.html, 4 pages.

"Measuring Orthostatic Blood Pressure", Tip Sheet: Measuring Orthostatic Blood Pressure, Mar. 7, 2016.

* cited by examiner

AUTOMATED ORTHOSTATIC HYPOTENSION ASSESSMENT

BACKGROUND

Patients in care facilities, such as hospitals, clinics, nursing homes, and the like, are often in compromised medical conditions. Injuries sustained by patients in care facilities result in significant healthcare costs. In an effort to prevent such injuries, various protocols are implemented to mitigate the risks. For example, patients who are at risk of falling when moving unassisted may be identified as fall risks, and certain systems may be implemented to reduce the opportunity for the patients to move about the room unassisted.

Orthostatic hypotension is a major risk factor that increases the likelihood of a patient fall. Orthostatic hypotension is defined as a sustained drop in blood pressure exceeding 20 mmHg systolic or 10 mm Hg diastolic occurring within 3 minutes of assuming upright posture. Orthostatic Hypotension can result in reduced blood flow to the brain, causing dizziness, nausea, syncope, and falls. Without advanced warning, the caregiver has no way of knowing that a patient may be susceptible to orthostatic hypotension.

Orthostatic hypotension can be assessed manually with a great deal of labor. For example, the typical assessment requires a blood pressure reading while laying, followed by sitting and another blood pressure reading after a wait, and finally standing and another blood pressure reading following a wait. This laborious process results in low compliance rates, and opportunities are lost to fully assess and mitigate a potentially devastating patient fall.

SUMMARY

In one aspect, a system for automatically assessing orthostatic hypotension for a patient supported on a patient support apparatus, comprises: at least one processor; and memory encoding instructions which, when executed by the at least one processor, cause the at least one processor to: receive position data identifying a first position of a patient supported on a patient support apparatus, and after a delay, receive vital signs data of the patient; receive position data identifying a second position of the patient supported on the patient support apparatus, and after a delay, receive vital signs data of the patient; determine an orthostatic hypotension assessment based on a difference in the vital signs data between the first and second positions; and based on the orthostatic hypotension assessment, modify one or more conditions on the patient support apparatus to mitigate a risk for patient fall.

In another aspect, a non-transitory computer readable storage medium having stored thereon computer readable instructions that, when read and executed by a computing device, cause the computing device to: receive position data identifying a first position of a patient supported on a patient support apparatus, and after a delay, receive vital signs data of the patient; receive position data identifying a second position of the patient supported on the patient support apparatus, and after a delay, receive vital signs data of the patient; determine an orthostatic hypotension assessment based on a difference in the vital signs data between the first and second positions; and based on the orthostatic hypotension assessment, modify one or more conditions on the patient support apparatus to mitigate a risk for patient fall.

In another aspect, a method for automatically assessing orthostatic hypotension comprises: receiving position data identifying a first position of a patient supported on a patient support apparatus, and after a delay, receiving vital signs data of the patient; receiving position data identifying a second position of the patient supported on the patient support apparatus, and after a delay, receiving vital signs data of the patient; determining an orthostatic hypotension assessment based on a difference in the vital signs data between the first and second positions; and based on the orthostatic hypotension assessment, modifying one or more conditions on the patient support apparatus to mitigate a risk for patient fall.

These and other aspects and embodiments are described in detail below, in relation to the attached drawing figures.

DETAILED DESCRIPTION

Figure 1:
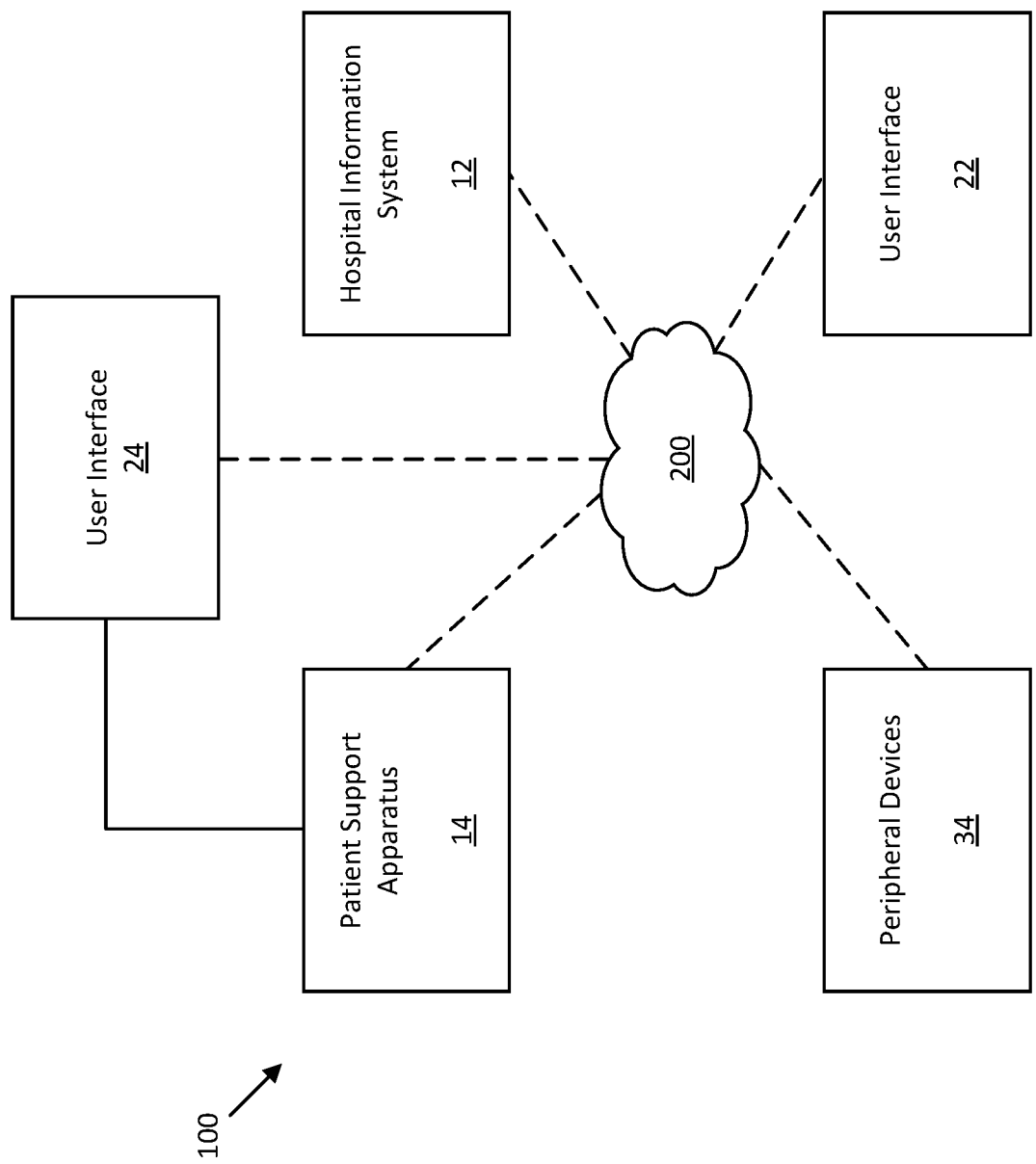
FIG. 1 illustrates an example automated orthostatic hypotension assessment system.

Various embodiments and advantages are explained more fully with reference to the non-limiting examples that are described and illustrated in the accompanying drawings and detailed in the following description. The features illustrated in the drawings are not necessarily drawn to scale, and features of one embodiment may be employed with other embodiments, even if not explicitly stated herein.

The examples used herein are intended merely to facilitate an understanding of ways in which the claimed subject matter may be practiced and to enable those of skill in the art to practice the embodiments of the claimed subject matter described herein. The embodiments provided herein are merely illustrative and should not be construed as limiting the scope of the claimed subject matter, which is defined solely by the appended claims. Also, like reference numerals may represent similar parts throughout the several views of the drawings.

FIG. 1 schematically illustrates an automated orthostatic hypotension assessment system 100. As shown in FIG. 1, the system 100 includes a patient support apparatus 14, one or more peripheral devices 34, a hospital information system 12, and one or more user interfaces 22, 24 each connected to a cloud server 200.

In some example embodiments, the patient support apparatus 14 referenced below will be referred to below as a "bed" such as a hospital bed. In alternative embodiments, the patient support apparatus 14 may be a chair, a recliner, or any other patient support apparatus. The patient support apparatus 14 may be located in a patient care facility, such as but not limited to a hospital, clinic, nursing home, and the like. Also, it is contemplated that the patient support apparatus 14 may be located in the patient's home.

The patient support apparatus 14 monitors the patient's motion and measures the patient's weight. In some examples, patient support apparatus 14 generates an alert when it is detected based on the motion data that the patient is exiting the patient support apparatus 14 without authorization. The alerts and data measured by the patient support apparatus 14, including the motion and weight data, is transferred to the cloud server 200.

The peripheral device 34 continually measures one or more vital signs of a patient supported on the patient support apparatus 14. In some example embodiments, the peripheral device 34 continually measures the blood pressure of the patent. Alternatively, or in addition to measuring blood pressure, the peripheral device 34 may also continually measure the heart rate of the patient and also including heart rhythm and other heart characteristics including ballistocardiography, ECG, heart rate variability, and the like.

The vital signs data measured by the peripheral device 34 is transferred to the cloud server 200. In some example embodiments, in addition to the transferring the vital signs data to the cloud server 200 or as an alternative, the peripheral device 34 also transfers the vital signs data to the patient support apparatus 14.

In some embodiments, the peripheral device 34 is a wearable device such as a specialized vital signs patch (VSP). In some embodiments, the peripheral device 34 is an ambulatory electrocardiography devices such as a Holter monitor. In some embodiments, the peripheral device 34 is a mattress pad device that can be placed under a mattress of patient support apparatus 14. In some embodiments, the peripheral device 34 is a spot monitor.

The hospital information system 12 stores a plurality of electronic medical records (EMRs). Each EMR contains the medical and treatment history of a patient admitted to the healthcare facility. The hospital information system 12 can receive the vital signs data measured from the peripheral device 34 via the cloud server 200.

The user interface 22 is part of a workstation such as a personal computing device or a dedicated peripheral computing device. In some examples, the workstation is a portable computing device such as a smartphone, laptop, tablet computer, and the like. In some examples, the workstation is a stationary desktop computer.

In some embodiments, the automated orthostatic hypotension assessment system 100 is hosted over the Internet. In this example embodiment, the automated orthostatic hypotension assessment system 100 is accessible from the user interface 22 via a web portal that provides a single sign-on configuration application.

In alternative embodiments, the automated orthostatic hypotension assessment system 100 is part of a local area network and is stored onsite. In this example, the automated orthostatic hypotension assessment system 100 is accessible from the user interface 22 via an intranet portal that provides a single sign-on configuration application.

The user interface 24 is operatively connected to the patient support apparatus 14. In some example embodiments, the user interface 24 is positioned on the patient support apparatus 14. In the example illustrated in FIG. 1, in addition to being connected to the patient support apparatus 14, the user interface 24 is also connected to the cloud server 200. In some embodiments, the automated orthostatic hypotension assessment system 100 is accessible from the user interface 24 positioned on the patient support apparatus 14.

Figure 2:
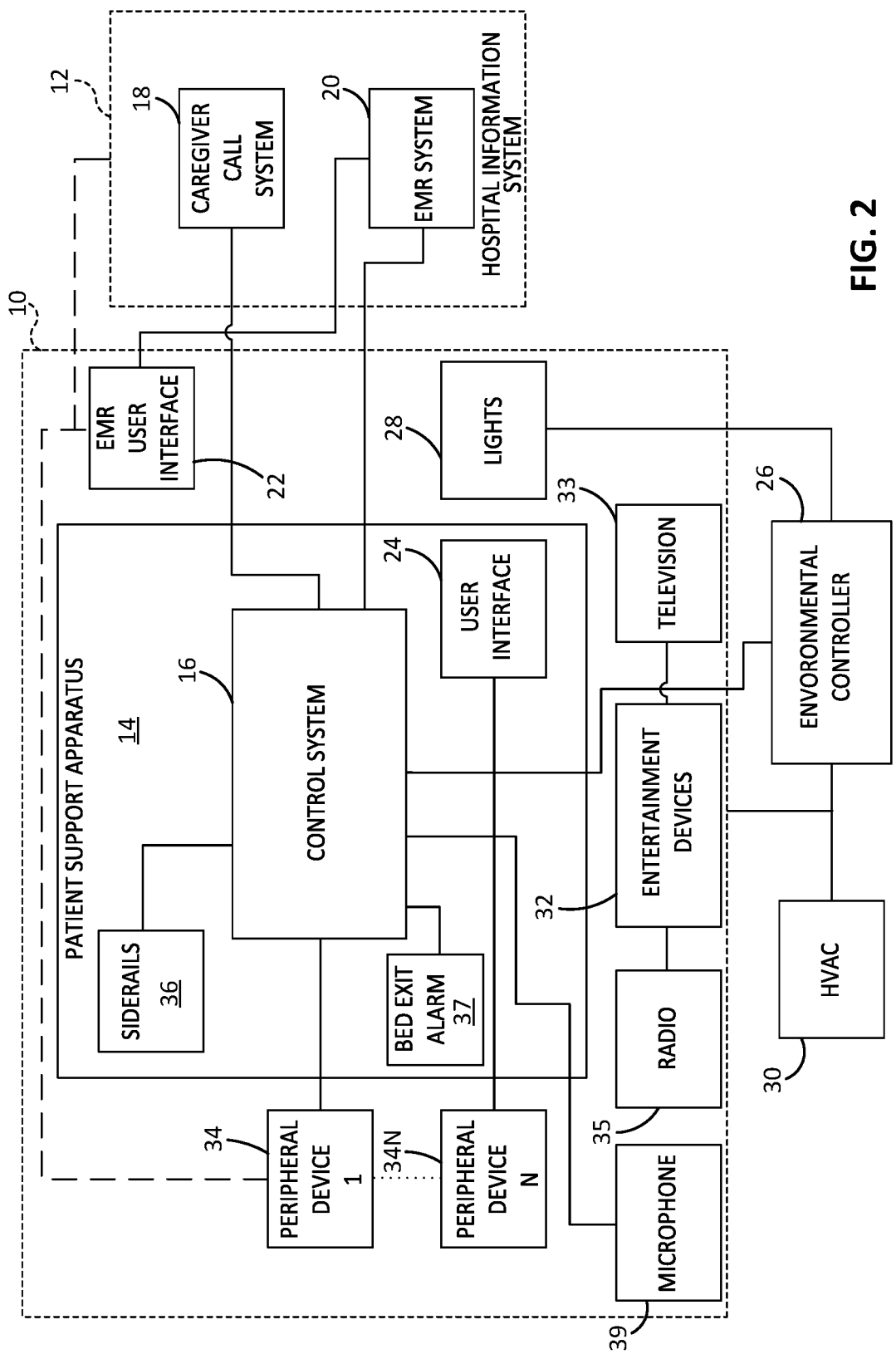
FIG. 2 is a detailed schematic diagram of a patient support apparatus and a hospital information system of the automated orthostatic hypotension assessment system of FIG. 1.

FIG. 2 is a detailed schematic diagram of the patient support apparatus 14 and hospital information system 12. In FIG. 2, the patient support apparatus 14 is positioned in a room 10 of a care facility according to one embodiment. This exemplary embodiment is provided here as one example of an environment in which the patient support apparatus 14 may be positioned and used. It is not intended to be limiting but only exemplary.

The hospital information system 12 includes a caregiver call system 18 and an electronic medical records (EMR) system 20. The caregiver call system 18 and EMR system 20 store information and data of a patient (not shown) that is supported on the patient support apparatus 14. The caregiver call system 18 and EMR system 20 receive and store patient data from the patient support apparatus 14 and one or more peripheral devices 34. The patient data is continuously updated as new patient data is received by the caregiver call system 18 and EMR system 20 from the patient support apparatus 14 and peripheral devices 34.

The EMR system 20 is accessible by a caregiver via the user interface 22 to input new patient information and data, and to enter orders. The user interface 22 may be provided on a plurality of workstations used throughout a facility to provide access to the EMR system 20.

The patient support apparatus 14 includes the control system 16 in communication with the caregiver call system 18 and the EMR system 20 through the cloud server 200. The control system 16 includes a user interface 24 that is used by the patient supported on the patient support apparatus 14 or a caregiver to provide inputs or display outputs.

The user interface 24 is operatively connected to the patient support apparatus 14. In some embodiments, the user interface 24 is positioned on the patient support apparatus 14. In further embodiments, the patient support apparatus 14 is in communication with the EMR system 20 via the control system 16, and acts as a peripheral device to the EMR system 20.

The control system 16 is in further communication with an environmental systems controller 26 which provides an interface between the patient support apparatus 14 and various environmental systems in the room 10 including lights 28, heating-ventilating-air-conditioning (HVAC) system 30, and entertainment devices 32 such as a television 33 or radio 35. The environmental systems controller 26 provides information and data to the control system 16 and acts on instructions from the control system 16 to modify operation of the various environmental systems in the room 10. The information and data from the environmental systems controller 26 is stored in memory associated with the environmental systems controller 26, and is updated as the conditions in the room 10 change.

In some embodiments, the control system 16 is operatively connected to a microphone 39 that can be used by the system 100 to record audible sounds from the patient. For example, after the patient transitions from a lying flat position to an inclined position, or from the inclined position to a standing up position, the patient can audibly indicate whether they feel dizzy, faint, light headed, or have blurred vision, disorientation, confusion, weakness, fatigue, chest pain, and the like, and the microphone 39 can be used by the system 100 to record the patient's audio response to changing their position.

The control system 16 is also operatively connected to the one or more peripheral devices 34 positioned in the room 10.

The peripheral device 34 continually measure one or more vital signs of the patient supported on the patient support apparatus 14. The peripheral device 34 transfer the one or more vital signs measurements to the control system 16.

Information and data used by the control system 16 may be stored in a memory of a peripheral device 34, including the measured vital signs. In some examples, the information and data used by the control system 16 is stored in a memory of the hospital information system 12. In further examples, the peripheral devices 34 may communicate with the control system 16, and the control system 16 stores the information and data from the peripheral devices 34 in a memory of the patient support apparatus 14. In further examples, the peripheral devices 34 may communicate to the control system 16 via a network connection such as a controller area network (CAN), and information and data stored on the peripheral devices 34 including the measured vital signs is accessible by the control system 16. Also, the peripheral devices 34 may be in direct communication with the hospital information system 12 without having to pass through the patient support apparatus 14.

The caregiver call system 18 generates alerts to notify caregivers of conditions based on signals from the control system 16 and information from the peripheral devices 34 and EMR system 20. The patient support apparatus 14 may also provide a communication link, such as audio or video communications, between a patient supported on the patient support apparatus 14 and the caregiver call system 18. In some instances, the caregiver call system 18 is an alert communication manager, or similar type of system.

Communication badges, that include telephone or other voice communication capability, may also be worn by caregivers to provide a direct communication between the caregivers and the patient. In this way, the caregiver call system 18 acts as a dispatch system to provide instructions to caregivers when various conditions warrant an intervention by the caregiver to respond to the needs of a particular patient.

The patient support apparatus 14 further includes siderails 36 that can be deployed to prevent the patient from exiting the patient support apparatus 14. In some embodiments, the siderails 36 are operatively connected to and controlled by the control system 16 to move from a stowed position to a deployed position based on an orthostatic hypotension assessment determined by the system 100. When in the deployed position, the siderails 36 can be used by the system 100 to mitigate a risk for patient fall such as by preventing the patient from exiting the patient support apparatus 14.

The patient support apparatus 14 further includes a bed exit alarm 37 that can be activated to monitor and prevent the patient from exiting the patient support apparatus 14. In some embodiments, the bed exit alarm 37 is operatively connected to and controlled by the control system 16 to transition from a non-activated state to an activated state based on an orthostatic hypotension assessment determined by the system 100. When in the activated state, the bed exit alarm 37 can be used by the system 100 to mitigate a risk for patient fall such as by sending an alert or notification to a caregiver when it is detected that the patient is attempting to exit the patient support apparatus 14.

Figure 3:
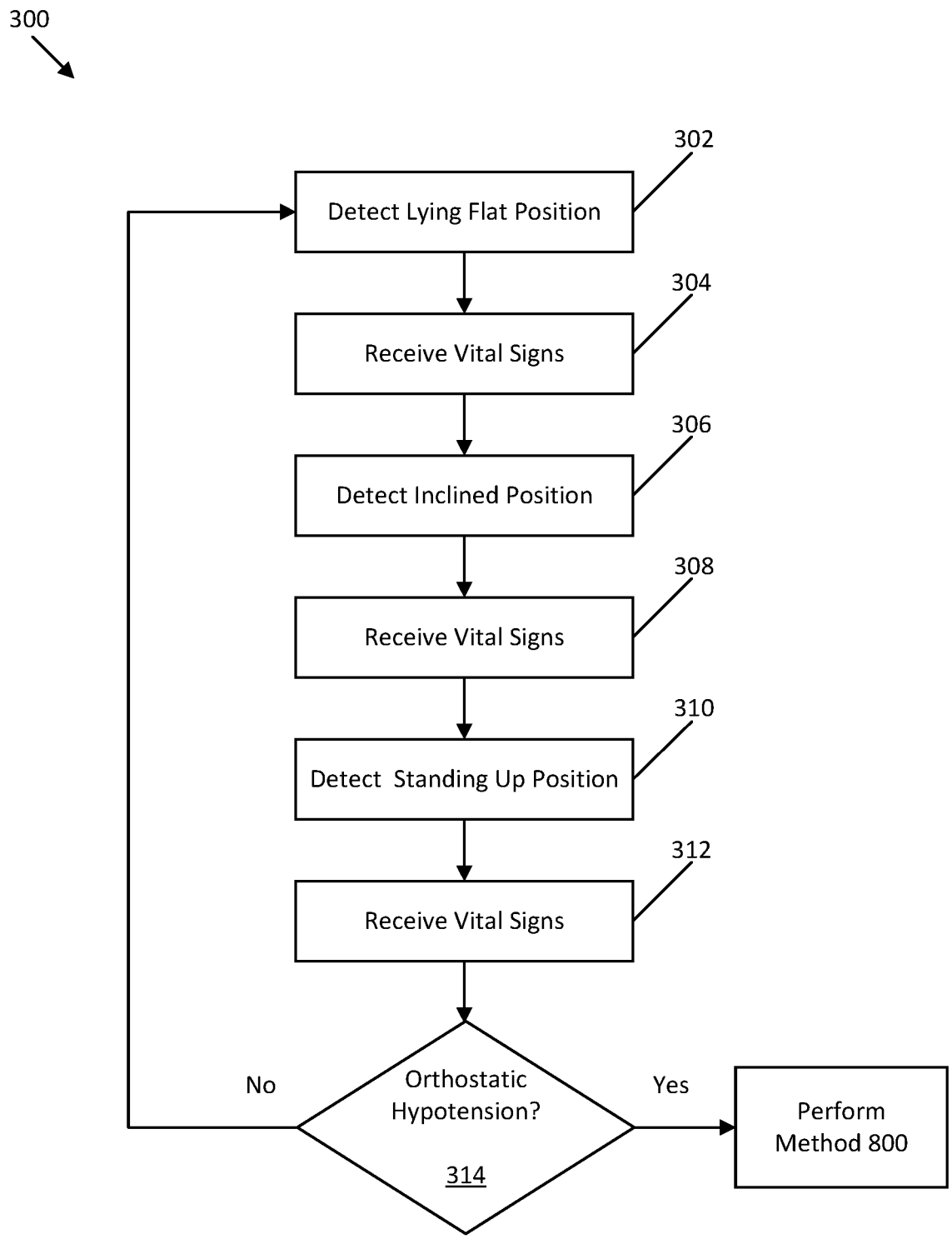
FIG. 3 illustrates a method of automatically assessing orthostatic hypotension.

FIG. 3 illustrates a method 300 for automatically assessing orthostatic hypotension that utilizes the automated orthostatic hypotension assessment system 100. The method 300 is non-interventional meaning that the method 300 does not interrupt the routine of a patient. Rather, the method 300 assesses orthostatic hypotension by passively measuring vital signs data and position data of the patient supported on the patient support apparatus 14.

Figure 4:
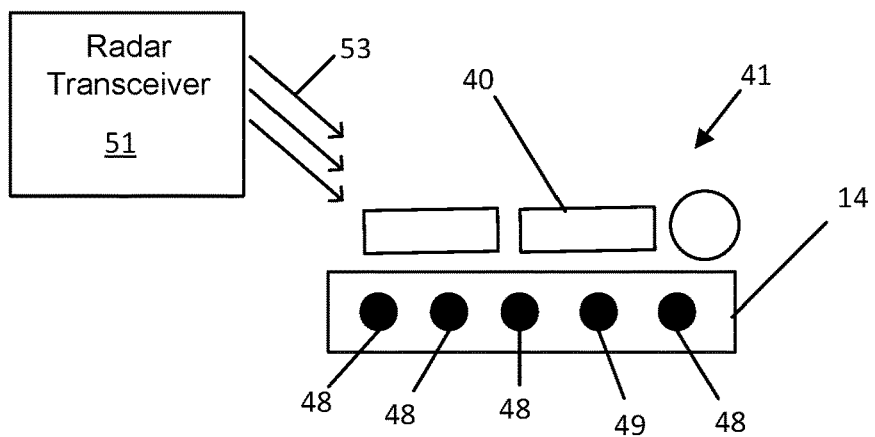
FIG. 4 illustrates a patient in a lying flat position on the patient support apparatus.
Figure 5:
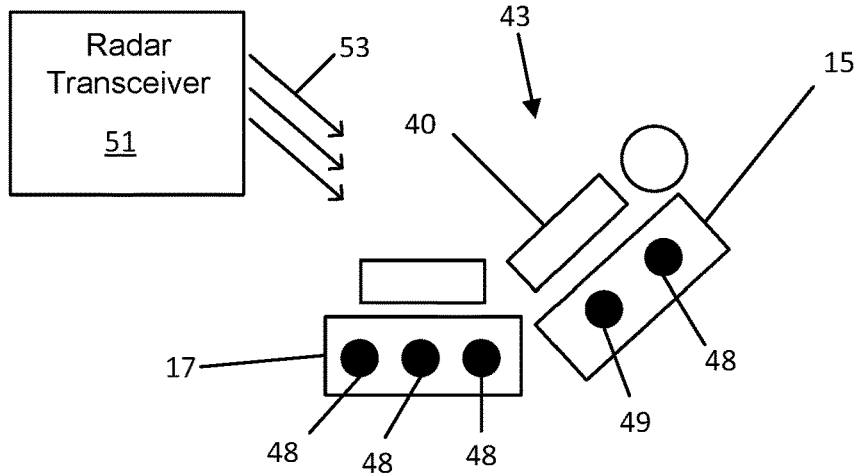
FIG. 5 illustrates a patient in an inclined position on the patient support apparatus.
Figure 6:
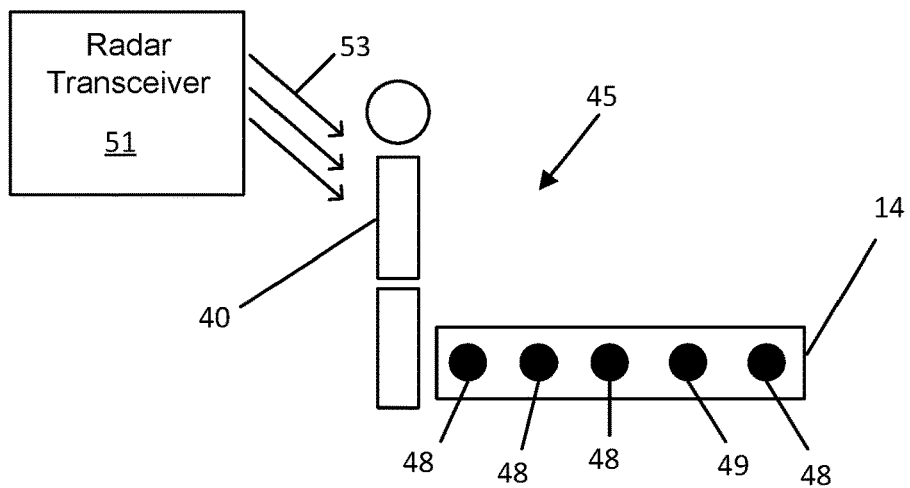
FIG. 6 illustrates a patient in a standing up position next to the patient support apparatus.

FIG. 4 illustrates a patient 40 in a lying flat position 41 on the patient support apparatus 14. FIG. 5 illustrates the patient 40 in an inclined position 43 on the patient support apparatus 14. FIG. 6 illustrates the patient 40 in a standing up position 45.

Referring now to FIGS. 3-6, the method 300 includes a step 302 of detecting the patient 40 in the lying flat position 41 on the patient support apparatus 14; a step 304 of receiving vital signs data after a predetermined amount of time has passed; a step 306 of detecting a change in the position of the patient 40 from the lying flat position 41 to the inclined position 43; a step 308 of receiving vital signs data after a predetermined amount of time has passed; a step 310 of detecting a change in the position of the patient 40 from the inclined position 43 to the standing up position 45; a step 312 of receiving vital signs data after a predetermined amount of time has passed; and a step 314 of determining whether the patient 40 has orthostatic hypotension based on the received vital signs data.

In some embodiments, the step 314 of determining whether the patient 40 exhibits orthostatic hypotension is based on steps 302-312. In some embodiments, steps 310 and 312 are optional such that the step 314 of determining whether the patient 40 exhibits orthostatic hypotension is based on steps 302-308 without performing steps 310 and 312. In some embodiments, steps 302 and 304 are optional such that the step 314 of determining whether the patient 40 exhibits orthostatic hypotension is based on steps 306-312 without performing steps 302 and 304. In yet some further embodiments, steps 306 and 308 are optional such that the step 314 of determining whether the patient 40 exhibits orthostatic hypotension is based on steps 302, 304, 310, and 312 without performing steps 306 and 308.

In some embodiments, steps 302-314 are performed sequentially. In other embodiments, steps 302-314 are not performed sequentially. For example, steps 310 and 312 can be performed before steps 306 and 308. Similarly, steps 306 and 308 can be performed before steps 302 and 304. As an illustrative example, the method 300 can include first detecting that the position of the patient 40 has changed from the inclined position to the standing up position (step 310) and then receiving vital signs measured after a predetermined amount of time (step 312) before detecting that the position of the patient 40 has changed from the lying flat position to the inclined position (step 306) and then receiving vital signs measured after a predetermined amount of time (step 308).

As shown in FIG. 3, when it is determined that the patient 40 does not have orthostatic hypotension (i.e., "No" in step 314), the method 300 can repeat steps 302-314 to continually assess orthostatic hypotension for the patient 40. Also, steps 302-314 can be repeated to determine trends in the measured vital signs over time such as an improvement in orthostatic hypotension or a deterioration in orthostatic hypotension.

Figure 8:
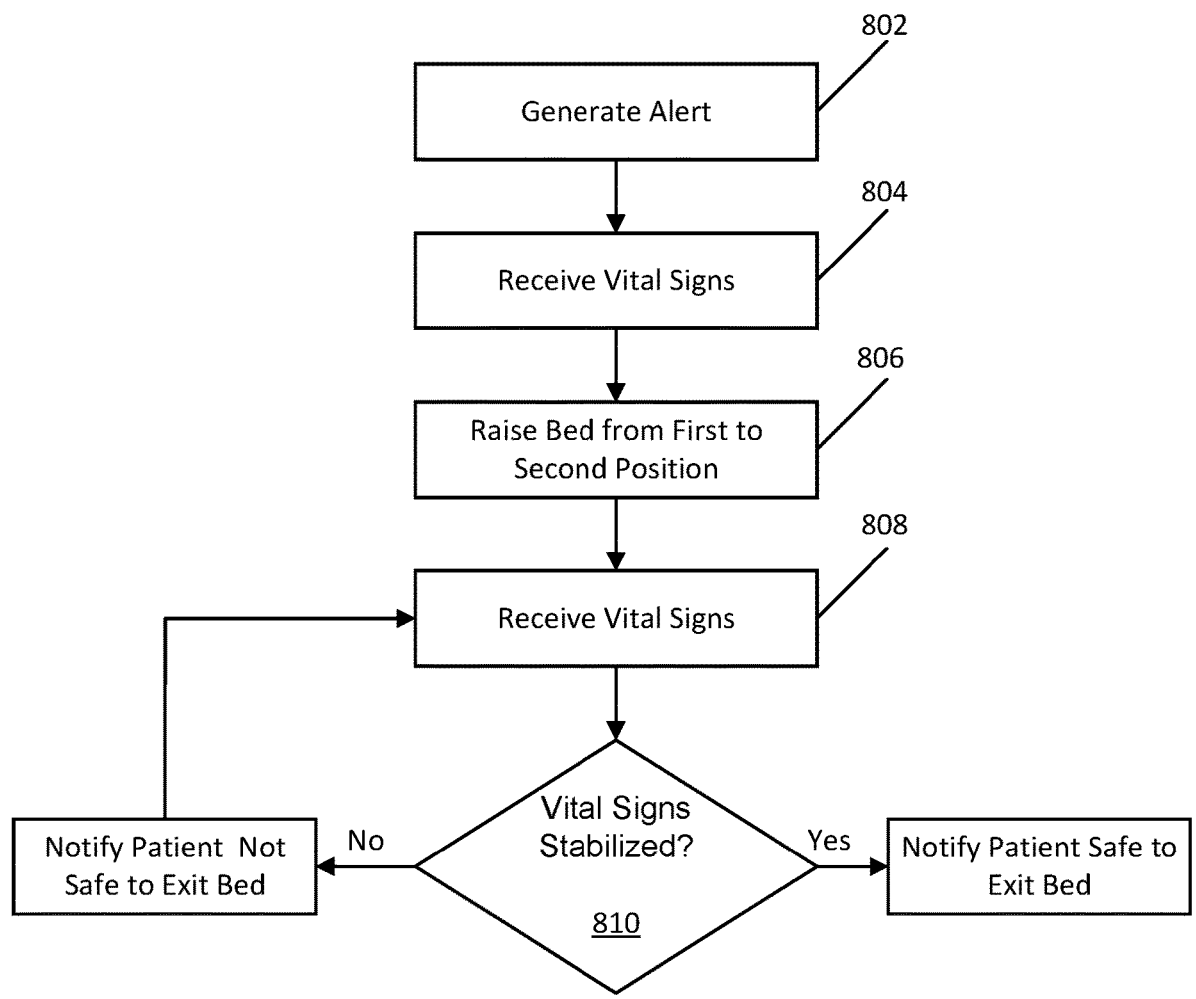
FIG. 8 illustrates a method of mitigating orthostatic hypotension risks.

When it is determined that the patient has orthostatic hypotension (i.e., "Yes" in step 314), a method 800, which is described in more detail with reference to FIG. 8, is performed to mitigate the risks associated with the orthostatic hypotension assessment.

In steps 302, 306, 310, position data is passively measured by one or more sensors such that the position data is measured without an intervention from a caregiver. In some embodiments, such as shown in FIGS. 4-6, the patient support apparatus 14 includes one or more sensors 48 that detect shifts in the weight of the patient 40 while supported on the patient support apparatus 14 to determine the position data. The one or more sensors 48 each generate an electrical signal that has a magnitude directly proportional to the weight or force being measured. The one or more sensors 48 may include one or more load cells, force transducers, or pressure transducers positioned on the patient support apparatus 14. The load cells may include hydraulic, pneumatic, and strain gauge load cells. In one example, the one or more sensors 48 are positioned under a mattress of the patient support apparatus 14.

Additional types of sensors may also be used to passively measure the position data. For example, in some embodiments, one or more sensors 49 are used to measure an angle of one or more portions of the patient support apparatus 14 such as an angle of an upper portion 15 relative to a lower portion 17 of the patient support apparatus 14 (see FIG. 5) to determine the position of the patient 40 on the patient support apparatus 14. In some embodiments, the position data is detected by the one or more sensors 48 (e.g., load cells, force transducers, or pressure transducers), and the position data is offset or scaled by the one or more sensors 49 that detect an angle of a portion of the patient support apparatus 14.

In further embodiments, the position data is passively measured by a mattress pad device placed under a mattress of patient support apparatus 14. In further embodiments, the position data is measured by a wearable device worn by the patient 40 such as a specialized vital signs patch. In some further embodiments, the position data is measured by using radar to detect the position of the patient 40 without physically contacting the patient such as by using a radar transceiver 51 that directs radar signals 53 toward the patient 40 and patient support apparatus 14, and that receives reflected radar signals.

In steps 304, 308, and 312, the vital signs data is passively measured by peripheral devices 34 such that the vital signs data is measured without an intervention from a caregiver. In certain embodiments, the vital signs data is measured continuously. Alternatively, the vital signs data can be measured periodically such as every 5 seconds.

In some embodiments, the vital signs data is measured by a wearable device such as a specialized vital signs patch worn by the patient 40 that measures vital signs data. The specialized vital signs patch measures vital signs including blood pressure, heart rate, respiration, temperature, patient motion, and the like. In some embodiments, the vital signs data is measured by a non-wearable, non-contact device such as a mattress pad device placed under a mattress of patient support apparatus 14. In some further embodiments, the vital signs data is measured by a spot monitor connected to the patient 40.

Figure 10:
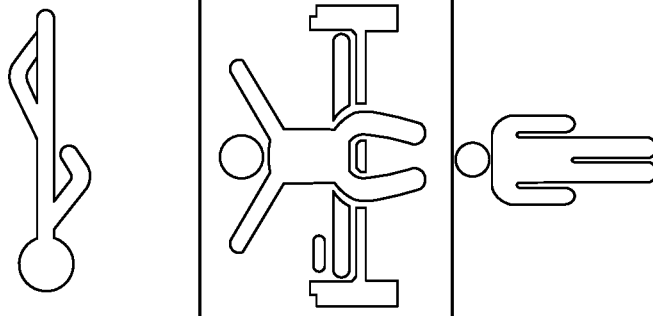
FIG. 10 illustrates a table that summarizes time intervals for measuring vital signs after a position of a patient is detected.

FIG. 10 illustrates a table that summarizes the amount of time that passes after the position of the patient 40 is detected before the vital signs are measured. For example, the vital signs data received in steps 304, 308, and 312 are vital signs that are measured after a delay of a predetermined amount of time has passed after the position of the patient 40 is detected. As shown in FIG. 10, in some examples, the vital signs data received in step 304 is measured after a delay of 3-5 minutes after detecting that the patient 40 is in the lying flat position 41. In some examples, the vital signs data received in step 308 is measured after a delay of 1-2 minutes after detecting that the patient 40 is in the inclined position 43. In some examples, the vital signs data received in step 312 is measured after a delay of 1-2 minutes after detecting that the patient 40 is in the standing up position 45.

Figure 7:
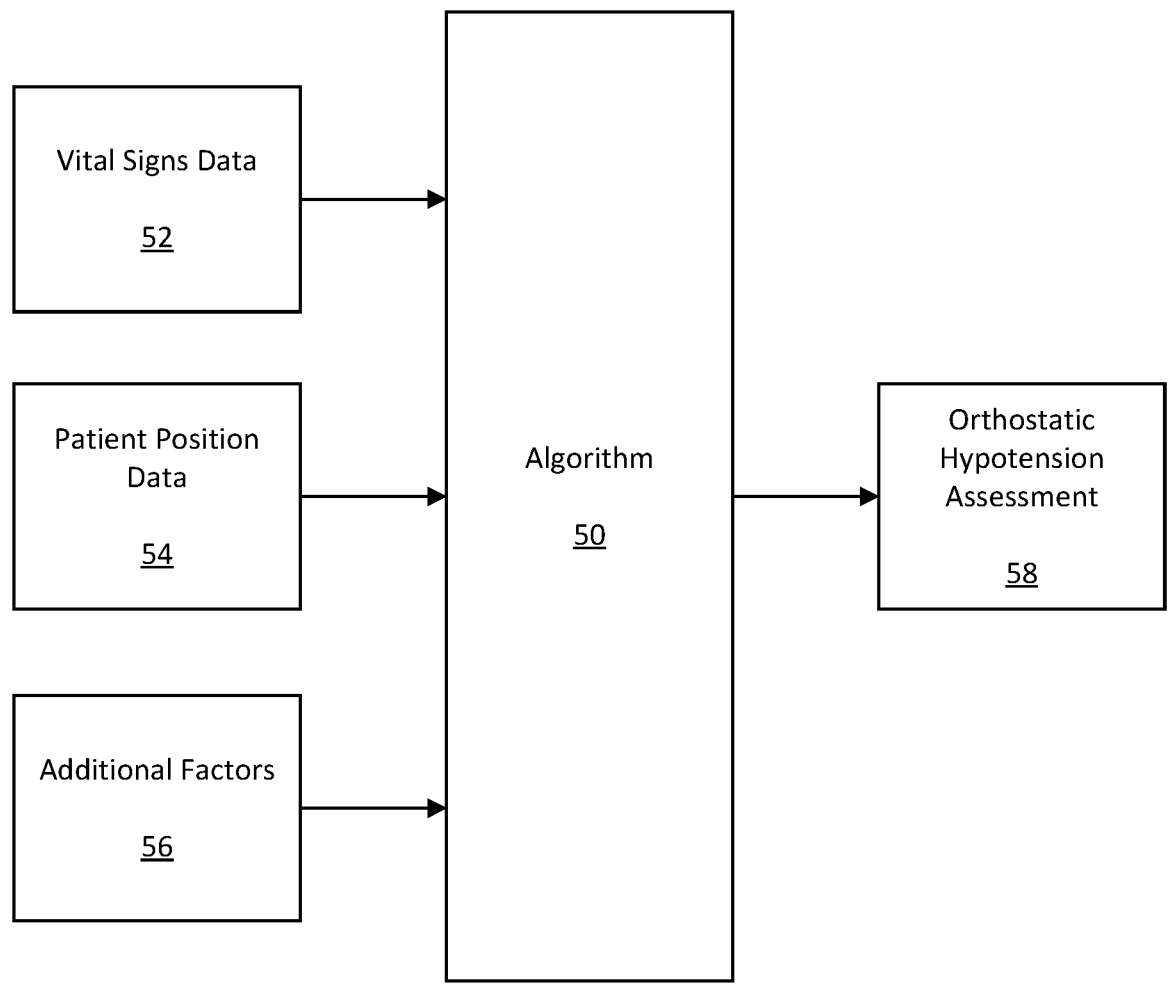
FIG. 7 schematically illustrates an algorithm performed by the automated orthostatic hypotension assessment system.

FIG. 7 schematically illustrates an algorithm 50 performed during step 314. The algorithm 50 can be stored in a memory of the cloud server 200 or in a memory of the patient support apparatus 14. As shown in FIG. 7, the algorithm 50 receives vital signs data 52, position data 54, and additional factors 56 as inputs. As described above, the vital signs data 52 and position data 54 are measured without intervention such that the routine of the patient 40 is not interrupted. As further shown in FIG. 7, the algorithm 50 generates an orthostatic hypotension assessment 58 as an output that is determined based on the vital signs data 52, position data 54, and additional factors 56.

The algorithm 50 correlates the vital signs data 52 to the position data 54 by correlating a first set of vital signs data 52 to a first set of position data identifying the patient 40 in the lying flat position 41, correlating a second set of vital signs data 52 to a second set of position data identifying the patient 40 in the inclined position 43, and correlating a third set of vital signs data 52 to a third set of position data identifying the patient 40 in the standing up position 45. The algorithm 50 also correlates the additional factors 56 to the position data 54 in a similar fashion.

In some embodiments, the vital signs data 52 obtained in steps 304, 308, and 312 is blood pressure such that the algorithm 50 utilizes differences in blood pressure from when the patient 40 is in the lying flat position 41, when the patient 40 is in the inclined position 43, and when the patient 40 is in the standing up position 45. The algorithm 50 determines a orthostatic hypotension assessment when there is a decrease greater than or equal to 20 mm Hg in systolic blood pressure, or a decrease greater than or equal to 10 mm Hg in diastolic blood pressure between the lying flat position 41 and the inclined position 43, or between the inclined position 43 and the standing up position 45.

When blood pressure measurements are not available, passively measured heart rate data is received in steps 304, 308, and 312. In such embodiments, the algorithm 50 utilizes differences in heart rate from when the patient 40 is in the lying flat position 41, when the patient 40 is in the inclined position 43, and when the patient 40 is in the standing up position 45. The algorithm 50 determines orthostatic hypotension when the rise in heart rate after standing is less than a threshold amount. In some embodiments, the algorithm 50 also determines that the patient has hypovolemia independent of whether the patient has orthostatic hypotension when a heart rate increase of at least 30 beats per minute is detected after three minutes have passed after transition from the inclined position 43 to the standing up position 45. In some example embodiments, in addition to or as an alternative to utilizing differences in heart rate, the algorithm 50 uses differences in heart rhythm, ballistocardiography, ECG, and/or heart rate variability to determine orthostatic hypotension with respect to the change in position of the patient 40.

In addition to comparing the differences in the vital signs data after the patient 40 has changed positions, the algorithm 50 may also utilize additional factors 56 such as patient symptoms after transitioning from the lying flat position 41 to the inclined position 43, or from the inclined position 43 to the standing up position 45. The symptoms may include dizziness, feeling faint, light headedness, blurred vision, disorientation and confusion, weakness, fatigue, chest pain, and the like. As described above, the algorithm can correlate the additional factors 56 to the position data 54.

In some embodiments, the additional factors 56 are inputted into the system 100 by the patient 40 or a caregiver using the user interface 24 positioned on the patient support apparatus 14. In further embodiments, the system 100 can receive the additional factors 56 by using a microphone 39 (see FIG. 2) to record audible responses from the patient 40 after the patient 40 transitions from the lying flat position 41 to the inclined position 43, or from the inclined position 43 to the standing up position 45.

In some embodiments, the vital signs data 52, position data 54, and additional factors 56 are transferred to the cloud server 200, and the algorithm 50 is performed by the cloud server 200. In such embodiments, the orthostatic hypotension assessment 58 is transferred from the cloud server 200 to the user interface 22 that is part of a workstation accessible by a caregiver such as a personal or dedicated computing device including portable computing devices such as smartphones, tablet computers, or laptops, and stationary desktop computers. Alternatively, or in addition to transferring the orthostatic hypotension assessment 58 to the user interface 22, the cloud server 200 may also transfer the orthostatic hypotension assessment 58 to the user interface 24 positioned on the patient support apparatus 14.

In some embodiments, the vital signs data 52 and position data 54 are received by the control system 16 of the patient support apparatus 14, and the algorithm 50 is performed by the control system 16. In such embodiments, the orthostatic hypotension assessment 58 is transferred directly from the control system 16 to the user interface 24 positioned on the patient support apparatus 14 without having to pass through the cloud server 200.

In some embodiments, the orthostatic hypotension assessment 58 is classified as a high risk, a medium risk, or a low risk of orthostatic hypotension. In other embodiments, the orthostatic hypotension assessment 58 is a positive or negative indication. In further embodiments, the orthostatic hypotension assessment 58 is determined as a score such as a score on a scale between 1 and 10 where 1 is low risk and 10 is high risk.

The orthostatic hypotension assessment 58 determined from the algorithm 50 can be used as an input in one or more protocols used by a care facility to mitigate the risk of the patient falling. For example, when the system 100 determines that the patient has a high risk of orthostatic hypotension, one or more siderails of the patient support apparatus 14 can be positioned from a stowed position to a deployed position to prevent the patient 40 from exiting the patient support apparatus 14. Additionally, or alternatively, a bed exit alarm of the patient support apparatus 14 can be activated by the system 100 when the system 100 determines that the patient has a high risk of orthostatic hypotension. Advantageously, the system 100 can use the orthostatic hypotension assessment 58 to improve risk stratification for patient falls in a care facility, and thereby mitigate patient falls.

Further, by correlating the vital signs data 52 and position data 54 (which are both measured without intervention and without interrupting the routine of the patient), orthostatic hypotension can be studied more efficiently and effectively. In some example embodiments, the system 100 can store the orthostatic hypotension assessment 58 in a patient electronic medical record (EMR) of the patient 40 that is located in to the EMR system 20.

In some embodiments, a falls risk model is built using the vital signs data 52, position data 54, additional factors 56, and orthostatic hypotension assessment 58. The model can then be used to calculate a falls risk score that indicates a fall risk for the patient.

FIG. 8 illustrates a method 800 of mitigating orthostatic hypotension risks. In some embodiments, the method 800 is performed after completion of the method 300 described above with reference to FIG. 3. For example, after it is determined in step 314 of the method 300 that the patient has orthostatic hypotension (i.e., "Yes" in step 314), the method 800 can be performed to reduce the risks associated with orthostatic hypotension.

Referring now to FIG. 8, the method 800 includes a step 802 of generating an alert; a step 804 receiving vital signs; a step 806 of raising the patient support apparatus 14 from a first position to a second position; a step 808 of receiving vital signs; and a step 810 of determining whether the vital signs have stabilized after a predetermined period of time after raising the bed. In some embodiments, the method 800 is an "easy rise mode."

In step 802, the orthostatic hypotension assessment 58 from the algorithm 50 triggers the system 100 to send an alert when it is determined that the patient 40 has orthostatic hypotension (i.e., "Yes" in step 314). In some examples, the alert is indicated on the user interface 22 and/or the user interface 24. The alert can be visual or auditory. In some embodiments, the alert is an audio transmission that emits from a speaker on the patient support apparatus 14. The audio transmission can include a message such as "Caution you are at risk for fall". Additional types of alerts, notifications, and messages may be generated by the system 100 in response to the orthostatic hypotension assessment 58.

In step 804, the vital signs of the patient 40 are received from one or more of the peripheral devices 34 described above. As described above, in some embodiments, the blood pressure of the patient 40 is measured by the peripheral devices 34. When blood pressure measurements are not available, in some embodiments, heart rate is measured.

In step 806, the patient support apparatus 14 is raised from a first position to a second position. In some examples, the first position is the lying flat position 41. In other examples, the first position is an intermediate position between the lying flat position 41 and the inclined position 43. In some examples, the second position is a position that enables the patient 40 to transition to the standing up position 45 such as an intermediate position between the inclined position 43 and the standing up position 45. In step 806, the patient 40 is gradually helped to their feet by angle changes in the patient support apparatus 14 in a gentle and slow manner appropriate for the patient's condition.

In step 808, the vital signs of the patient 40 are received from one or more of the peripheral devices 34 described above. As described above, in some embodiments, the blood pressure of the patient 40 is measured by the peripheral devices 34. When blood pressure measurements are not available, in some embodiments, heart rate is measured.

In step 810, when it is determined that the patient's vital signs have not stabilized (i.e., "No" in step 810), the system 100 notifies the patient 40 that it is not safe for the patient 40 to exit the patient support apparatus 14, and step 808 is repeated. When it is determined that the patient's vital signs have stabilized (i.e., "Yes" in step 810), the system 100 notifies the patient 40 that it is safe for the patient 40 to exit the patient support apparatus 14.

In some embodiments, the determination in step 810 is based on whether there is a decrease greater than or equal to 20 mm Hg in systolic blood pressure, or a decrease greater than or equal to 10 mm Hg in diastolic blood pressure before and after transitioning from the first position to the second position such that it is not safe for the patient 40 to exit the patient support apparatus 14. In some embodiments, the determination in step 810 is based on whether the increase in heart rate after standing is less than a threshold amount such that it is not safe for the patient to exit the patient support apparatus 14.

The method 800 slowly eases the patient 40 up to a standing position, and continuously supports and monitors the patient 40 such that only after the patient's vital signs have stabilized, is the patient 40 allowed to exit the patient support apparatus 14 and walk. In this manner, the method 800 reduces patient falls caused by dizziness and loss of consciousness associated with orthostatic hypotension.

Figure 9:
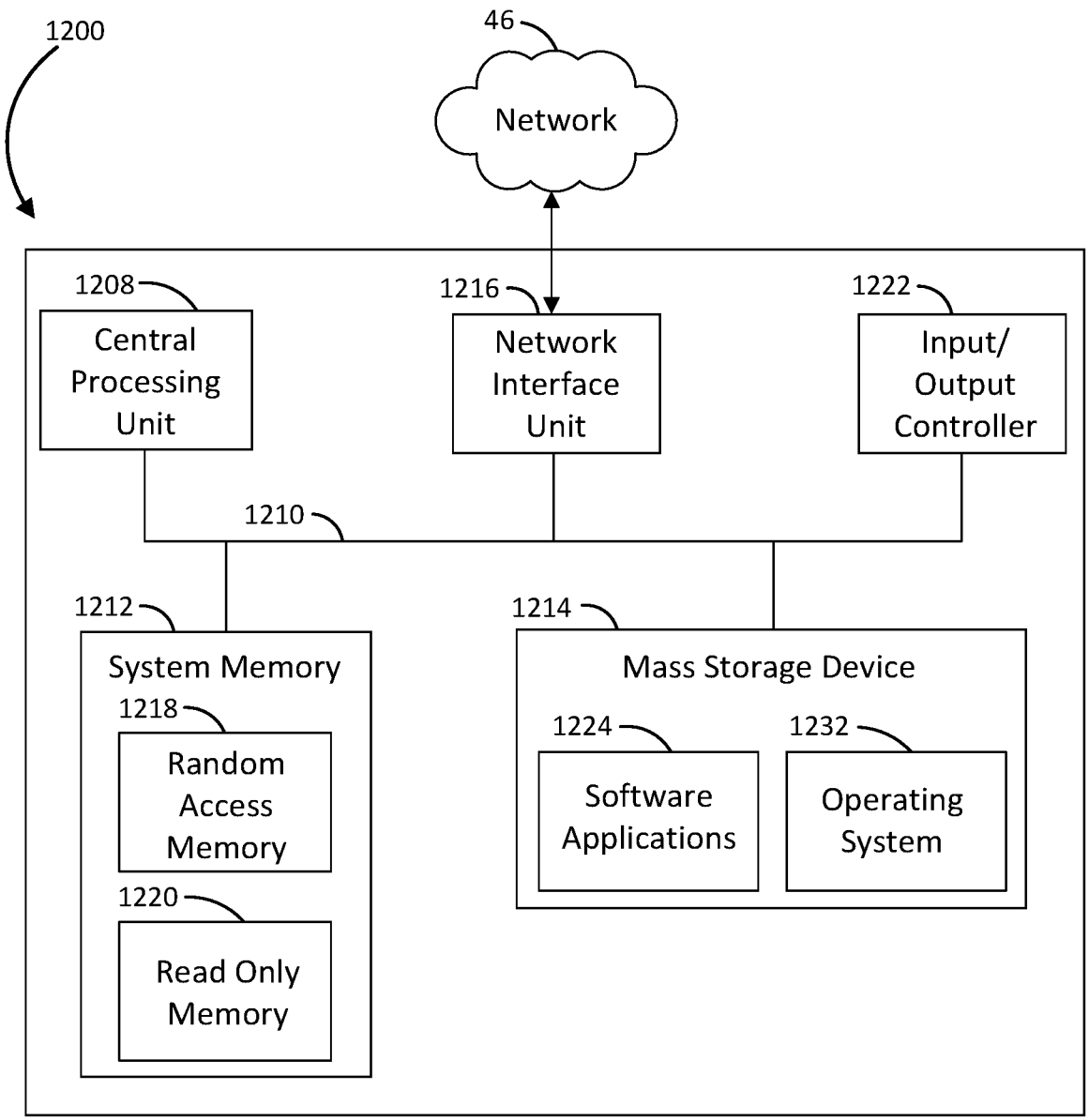
FIG. 9 illustrates example physical components of a computing device.

FIG. 9 illustrates example physical components of a computing device 1200, such as one that is associated with the control system 16 and cloud server 200. As illustrated, the computing device 1200 includes at least one processor or central processing unit ("CPU") 1208, a system memory 1212, and a system bus 1210 that couples the system memory 1212 to the CPU 1208. The central processing unit 1208 is an example of a processing device. The system memory 1212 includes a random access memory ("RAM") 1218 and a read-only memory ("ROM") 1220. A basic input/output system containing the basic routines that help to transfer information between elements within the computing device 1200, such as during startup, is stored in the ROM 1220. The computing device 1200 further includes a mass storage device 1214 able to store software instructions and data.

The mass storage device 1214 is connected to the CPU 1208 through a mass storage controller (not shown) connected to the system bus 1210. The mass storage device 1214 and its associated computer-readable data storage media provide non-volatile, non-transitory storage for the computing device 1200. Although the description of computer-readable data storage media contained herein refers to a mass storage device, such as a hard disk or CD-ROM drive, it should be appreciated by those skilled in the art that computer-readable data storage media can be any available non-transitory, physical device or article of manufacture from which the device can read data and/or instructions. The mass storage device 1214 is an example of a computer-readable storage device.

Computer-readable data storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid-state memory technology, CD-ROMs, digital versatile discs ("DVDs"), other optical storage media, magnetic cassettes, magnetic tape, magnetic disk storage or other magnetic storage devices, or any other medium which can be used to store the desired information and which can be accessed by the computing device 1200.

According to various embodiments, the computing device 1200 may operate in a networked environment using logical connections to remote network devices through the network 46, such as a local network, the Internet, or another type of network. The computing device 1200 connects to the network 46 through a network interface unit 1216 connected to the system bus 1210. The network interface unit 1216 may also be utilized to connect to other types of networks and remote computing systems. The computing device 1200 also includes an input/output controller 1222 for receiving and processing input from a number of other devices, including a keyboard, a mouse, a touch user interface display screen, or another type of input device. Similarly, the input/output controller 1222 may provide output to a touch user interface display screen, or other type of output device.

As mentioned above, the mass storage device 1214 and the RAM 1218 of the computing device 1200 can store software instructions and data. The software instructions can include an operating system 1232 suitable for controlling the operation of the computing device 1200. The mass storage device 1214 and/or the RAM 1218 also store software instructions, that when executed by the CPU 1208, cause the computing device 1200 to provide the functionality discussed in this document.

The use of the terms "a" and "an" and "the" and similar referents in the context of describing the subject matter (particularly in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Furthermore, the foregoing description is for the purpose of illustration only, and not for the purpose of limitation, as the scope of protection sought is defined by the claims as set forth hereinafter together with any equivalents thereof entitled to.

The use of any and all examples, or exemplary language (e.g., "such as") provided herein, is intended merely to better illustrate the subject matter and does not pose a limitation on the scope of the subject matter unless otherwise claimed. The use of the term "based on" and other like phrases indicating a condition for bringing about a result, both in the claims and in the written description, is not intended to foreclose any other conditions that bring about that result.

What is claimed is:

1. A system for automatically assessing orthostatic hypotension for a patient supported on a patient support apparatus, the system comprising:
   at least one processor; and
   memory encoding instructions which, when executed by the at least one processor, cause the at least one processor to:
   receive position data identifying a first position of a patient supported on a patient support apparatus, and after a delay, receive vital signs data of the patient;
   receive position data identifying a second position of the patient supported on the patient support apparatus, and after a delay, receive vital signs data of the patient;
   determine an orthostatic hypotension assessment based on a difference in the vital signs data between the first and second positions; and
   based on the orthostatic hypotension assessment, modify one or more conditions on the patient support apparatus to mitigate a risk for patient fall.

2. The system of claim 1, wherein the first position is a lying flat position, and the second position is an inclined position.

3. The system of claim 2, wherein the position data further identifies the patient in a third position, the third position being a standing up position, and the orthostatic hypotension assessment is determined based on differences in the vital signs data between the first, second, and third positions.

4. The system of claim 1, further comprising a wearable device, a non-wearable, non-contact device, or a spot monitor to measure the vital signs data.

5. The system of claim 1, further comprising one or more sensors that detect shifts in the weight of the patient on the patient support apparatus to determine the position data, the one or more sensors including one or more load cells, force transducers, or pressure transducers that are positioned on the patient support apparatus.

6. The system of claim 1, further comprising one or more sensors positioned on the patient support apparatus that detect an angle of one or more portions of the patient support apparatus to determine the position data.

7. The system of claim 1, wherein the position data is detected by one or more load cells, force transducers, or pressure transducers, and the position data is offset or scaled by one or more sensors that detect an angle of a portion of the patient support apparatus.

8. The system of claim 1, further comprising a cloud server that determines the orthostatic hypotension assessment, and the cloud server sends the orthostatic hypotension assessment for display on a user interface.

9. The system of claim 1, further comprising a control system on the patient support apparatus that determines the orthostatic hypotension assessment, and displays the orthostatic hypotension assessment on a user interface positioned on the patient support apparatus.

10. The system of claim 1, wherein the vital signs data is blood pressure, heart rate, heart rhythm, ballistocardiography, ECG, or heart rate variability.

11. The system of claim 1, wherein the memory encodes additional instructions which, when executed by the at least one processor, cause the at least one processor to:
    adjust a position of the patient support apparatus;
    after a delay, receive one or more vital signs of the patient;
    determine whether the vital signs of the patient stabilize; and
    when the vital signs do not stabilize, generate a message that notifies the patient that is not safe for the patient to exit the patient support apparatus.

12. A non-transitory computer readable storage medium having stored thereon computer readable instructions that, when read and executed by a computing device, cause the computing device to:
    receive position data identifying a first position of a patient supported on a patient support apparatus, and after a delay, receive vital signs data of the patient;
    receive position data identifying a second position of the patient supported on the patient support apparatus, and after a delay, receive vital signs data of the patient;
    determine an orthostatic hypotension assessment based on a difference in the vital signs data between the first and second positions; and
    based on the orthostatic hypotension assessment, modify one or more conditions on the patient support apparatus to mitigate a risk for patient fall.

13. The non-transitory computer readable storage media of claim 12, wherein modifying one or more conditions on the patient support apparatus includes deploying one or more siderails to prevent the patient from exiting the patient support apparatus.

14. The non-transitory computer readable storage media of claim 12, wherein modifying one or more conditions on the patient support apparatus includes activating a bed exit alarm on the patient support apparatus.

15. The non-transitory computer readable storage media of claim 12, wherein the first and second positions of the patient are detected by one or more sensors that detect shifts in the weight of the patient on the patient support apparatus.

16. A method for automatically assessing orthostatic hypotension, the method comprising:
    receiving position data identifying a first position of a patient supported on a patient support apparatus, and after a delay, receiving vital signs data of the patient;
    receiving position data identifying a second position of the patient supported on the patient support apparatus, and after a delay, receiving vital signs data of the patient;
    determining an orthostatic hypotension assessment based on a difference in the vital signs data between the first and second positions; and
    based on the orthostatic hypotension assessment, modifying one or more conditions on the patient support apparatus to mitigate a risk for patient fall.

17. The method of claim 16, further comprising:
    adjusting a position of the patient support apparatus;
    after a delay, receiving one or more vital signs of the patient;
    determining whether the vital signs of the patient stabilize; and
    when the vital signs do not stabilize, generating a message that notifies the patient that is not safe for the patient to exit the patient support apparatus.

18. The method of claim 16, wherein the vital signs data includes blood pressure, heart rate, heart rhythm, ballistocardiography, ECG, or heart rate variability.

19. The method of claim 16, wherein modifying one or more conditions on the patient support apparatus includes deploying one or more siderails on the patient support apparatus to prevent the patient from exiting the patient support apparatus.

20. The method of claim 16, wherein modifying one or more conditions on the patient support apparatus includes activating a bed exit alarm on the patient support apparatus.

* * * * *